United States Patent
Guillon et al.

(10) Patent No.: US 7,217,850 B2
(45) Date of Patent: May 15, 2007

(54) PROCESS FOR THE PRODUCTION OF PHENYLALKANES IN THE PRESENCE OF A SOLID ACID CATALYST THE DEACTIVATION OF WHICH IS DELAYED

(75) Inventors: Emmanuelle Guillon, Saint Genis Laval (FR); Eric Sanchez, Rueil Malmaison (FR); Patrick Briot, Pommier de Beaurepaire (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 553 days.

(21) Appl. No.: 10/840,364

(22) Filed: May 7, 2004

(65) Prior Publication Data

US 2004/0260133 A1    Dec. 23, 2004

(30) Foreign Application Priority Data

May 7, 2003    (FR) .................................... 03 05596

(51) Int. Cl.
*C07C 2/66* (2006.01)
(52) U.S. Cl. .................. 585/455; 585/449; 585/467
(58) Field of Classification Search .............. 585/455, 585/449, 467
See application file for complete search history.

(56) References Cited

U.S. PATENT DOCUMENTS 4,107,224 A * 8/1978 Dwyer ........................ 585/449
5,756,873 A * 5/1998 Ou .............................. 585/467

FOREIGN PATENT DOCUMENTS

EP    2795402    12/2000

* cited by examiner

*Primary Examiner*—Thuan D. Dang
(74) *Attorney, Agent, or Firm*—Millen, White, Zelano & Branigan, P.C.

(57) ABSTRACT

The invention relates to a process for the production of phenylalkanes comprising an alkylation reaction of at least one aromatic compound by at least one linear olefin having from 9 to 16 carbon atoms per molecule. Said reaction is carried out in a catalytic reactor in which n reaction zones are present each containing at least one same solid acid catalyst, n being greater than or equal to 2, and at the inlet to each of which at least one fraction of the total quantity of olefins necessary for said reaction is introduced. The phenylalkanes obtained by the process according to the invention are particularly suitable for manufacturing detergents.

19 Claims, 1 Drawing Sheet

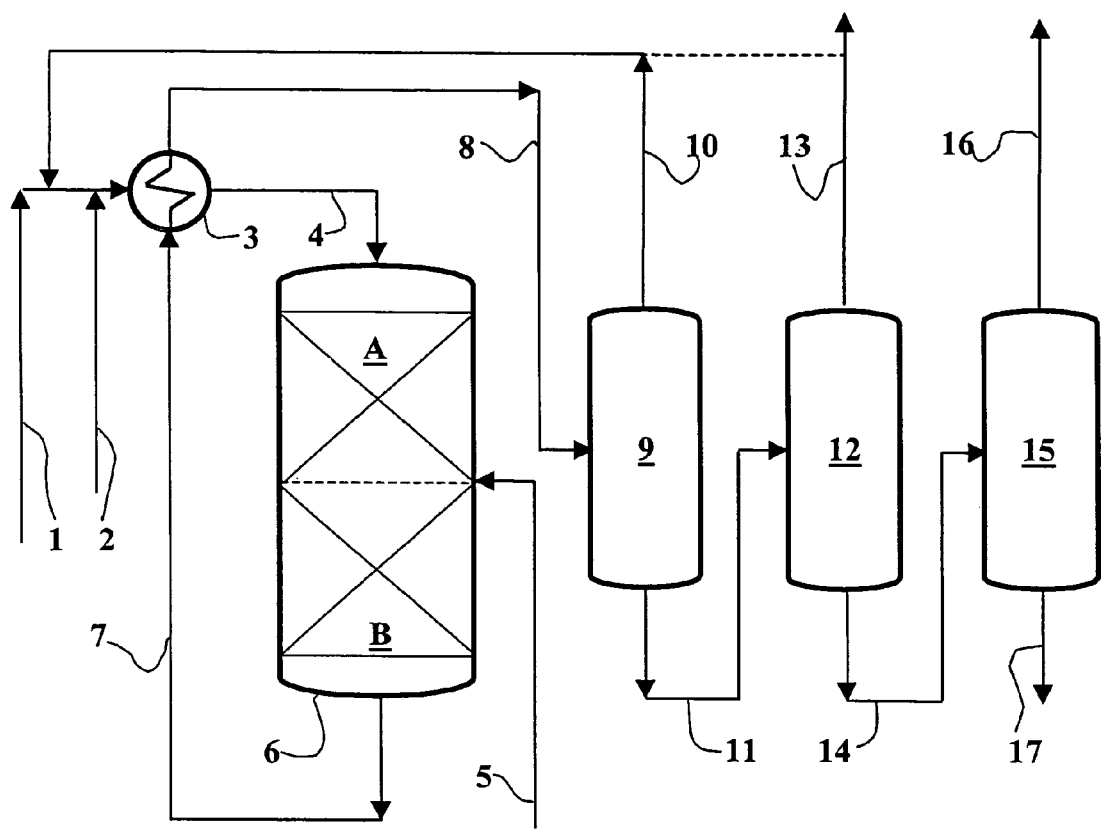

PROCESS FOR THE PRODUCTION OF PHENYLALKANES IN THE PRESENCE OF A SOLID ACID CATALYST THE DEACTIVATION OF WHICH IS DELAYED

TECHNICAL FIELD

The present invention relates to a process for the production of phenylalkanes by alkylation of at least one aromatic compound by means of olefinic hydrocarbons, most often linear and comprising in general from 9 to 16 carbon atoms per molecule in the presence of a solid acid catalyst. The phenylalkanes obtained according to the process of the invention constitute precursors of choice for the formulation of detergents and in particular certain biodegradable detergents, for example after sulphonation.

PRIOR ART

At present, the bases for biodegradable detergents largely require linear alkylbenzenes or phenylalkanes. The production of this type-of compounds is growing steadily. One of the main properties sought for these compounds, after a sulphonation stage, is, apart from their detergent power, their biodegradability. In order to ensure maximum biodegradability, the alkyl group must be linear and long and the distance between the sulphonate group and the terminal carbon of the linear chain must be maximal. Such compounds are obtained by alkylation of benzene with olefinic hydrocarbons, the most interesting of which are constituted by linear $C_9$–$C_{16}$, and preferably $C_{10}$–$C_{14}$ olefins.

The linear alkybenzenes generally obtained by alkylation of the benzene by means of linear olefin(s) are most often prepared by two known processes. The first process, described for example in Ullmann's Encyclopaedia 5th volume A 25 page 766, uses, at the benzene alkylation stage, hydrofluoric acid as acid catalyst. The second process, described for example in Ullmann's Encyclopaedia 5th volume A 25 page 766, uses a Friedel-Crafts type catalyst, generally based on $AlCl_3$. These two processes lead to the formation of 2-, 3-, 4-, 5- and 6-phenylalkane isomers. The main drawback of these processes is connected with environmental constraints. The first process, based on the use of hydrofluoric acid poses severe problems of safety on the one hand and waste reprocessing on the other. The second process poses the problem of waste resulting from the use of said Friedel-Crafts type catalysts. In fact it is necessary in this case to neutralize the effluents by a basic solution on leaving the reactor. Moreover, the separation of the catalyst from the reaction products is necessary and difficult-to implement for the two processes.

In order to resolve these drawbacks, it has been proposed to carry out alkylation of the benzene by linear olefins in the presence of a solid acid catalyst. The prior art reports the use of numerous solid acid catalysts for the synthesis of phenylalkanes. Said catalysts can be constituted by zeolithic compounds as defined in the classification of "Atlas of Zeolite Framework Types", W. M. Meier, D. h. Olson and Ch. Baerlocher, 5th revised edition, 2001, Elsevier, to which the present application also refers. Thus U.S. Pat. No. 4,301,317 proposes a series of zeolites including cancrinite, gmelinite, mordenite, offretite and ZSM-12. The Patent Application FR-A-2 697 246 teaches the use of catalysts based on dealuminated Y zeolite. The patent EP-B-160 144 discloses the use of Y zeolites the crystallinity of which varies from 30 to 80% whilst U.S. Pat. No. 5,036,033 teaches the use of Y zeolites rich in ammonium cations.

Amorphous catalysts can also be used, such as the silica-aluminas (U.S. Pat. No. 4,870,222, U.S. Pat. No. 5,344,997, U.S. Pat. No. 5,245,094) or catalysts based on supported heteropolyanions (CN 1,277,894, FR-A-2,828,486) or clays (U.S. Pat. No. 5,733,439, EP-A-0 711 600).

The solid acid catalysts constitute a useful alternative to the use of prior acid catalysts, in particular hydrofluoric HF acid, and Friedel-Crafts type catalysts. However, the major drawback of the solid acid catalysts is their rapid deactivation during the alkylation reaction by adsorption to the surface of said catalysts of hydrocarbon species.

Several patents have already taught solutions aimed at limiting or even preventing the deactivation of solid acid alkylation catalysts. For example, U.S. Pat. No. 5,648,579 discloses a continuous alkylation process in the presence of a solid acid catalyst the deactivation of which is prevented by carrying out alternately an alkylation reaction stage (benzene+olefins) and a stage of washing with pure benzene during which the flow of olefins is interrupted. U.S. Pat. No. 5,453,553 discloses a process for the production of linear alkylbenzenes in the presence of hydrogen with use of a solid catalyst comprising a metallic phase in close contact with a zeolite. These prior processes disclosed in U.S. Pat. No. 5,648,579 and U.S. Pat. No. 5,453,553 dispense with the regeneration of the solid acid catalyst or make it possible at least to keep the catalyst active over a long period (1 month). However, most of the prior production processes for phenylalkanes using a solid acid catalyst require the implementation of a stage of regeneration of the deactivated catalyst in order to release the hydrocarbon species adsorbed at the surface of said catalyst. This regeneration stage is disadvantageous as the alkylation reaction cycles are frequently interrupted in order to regenerate the deactivated catalyst. For example, the process for the alkylation of aromatic hydrocarbons disclosed in the patent EP-B1-0 353 813 comprises a periodic regeneration of the solid acid catalyst with flows of paraffins alternating with flows of alcohols for a period of up to 8 hours, the duration of the alkylation reaction cycle, being of the order of 12 hours.

The deactivation of the solid catalyst can also be delayed by an increase in the temperature of the alkylation reaction, but this increase in temperature is to the detriment of the linearity of the desired product. It is recommended, in view of their use as precursors for the formulation of detergents, to produce phenylalkanes having a linear alkyl group without branching.

Also, one of the objectives of the present invention is to provide a process for the production of phenylalkanes using a solid acid catalyst the deactivation of which is delayed in order to allow alkylation reaction cycle durations which are prolonged relative to those of the prior processes. Another objective of the present invention is to provide a process for the production of phenylalkanes the selectivity of which in linear products, i.e. not having any branchings on the alkyl chain carried by the benzene group, is improved.

SUMMARY AND BENEFIT OF THE INVENTION

The present invention relates to a process for the production of phenylalkanes comprising an alkylation reaction of at least one aromatic compound by at least one linear olefin having from 9 to 16 carbon atoms per molecule, said reaction being carried out in a catalytic reactor in which n reaction zones are present each containing at least one same solid acid catalyst, n being greater than or equal to 2, and at the inlet to each of which at least one fraction of the total quantity of olefins necessary for said reaction is introduced. Surprisingly and unexpectedly, the Applicant has discovered that such a process makes it possible to delay the deactivation of the solid acid catalyst. Thus, the duration of the alkylation reaction cycle is appreciably extended, and the stages of regeneration of the deactivated catalyst are less frequent than in the prior processes. The process according to the invention also has the advantage of producing phenylalkanes the selectivity of which in linear products, i.e. products not having any branchings on the alkyl chain carried by the benzene group, is improved, which is useful as such products are sought for a use in the formulation of detergents. Another advantage of the invention is the optimization of the quantity of aromatic compound(s), preferably benzene, to be introduced into the catalytic reactor for the alkylation reaction. Unlike the prior processes in which the whole quantity of olefins is generally introduced in one go, the process according to the invention makes it possible to reduce the quantity of benzene necessary relative to the prior products whilst maintaining a close (aromatic compound(s)/olefins) ratio, preferably (benzene/olefins), in the catalytic reactor.

BRIEF DESCRIPTION OF THE DRAWING

The FIGURE is a flow diagram the present process.

DESCRIPTION

The present invention relates to a process for the production of phenylalkanes comprising an alkylation reaction of at least one aromatic compound by at least one linear olefin having from 9 to 16 carbon atoms per molecule, said reaction being carried out in a catalytic reactor in which n reaction zones are present each containing at least one same solid acid catalyst, n being greater than or equal to 2, and at the inlet to each of which at least one fraction of the total quantity of olefins necessary for said reaction is introduced.

By "same solid acid catalyst" is meant a catalyst having the same nature and the same chemical composition in each of the n zones. For example, when the catalyst is a zeolitic catalyst containing a zeolite such as those described below in the present description, each of the n reaction zones contains a catalyst based on a zeolite of the same structural type and having the same chemical composition, i.e. the same X/T ratio, X being chosen from silicon and germanium, T being chosen from aluminium, iron, gallium, boron, titanium, vanadium, zirconium, molybdenum, arsenic, antimony, chromium and manganese.

The linear olefins used as alkylating agents preferably contain from 10 to 14 carbon atoms per molecule. The aromatic compound is preferably benzene. According to the invention, the process is preferably carried out in a single catalytic reactor, generally with a fixed bed, in which n reaction zones (n≧2) are present each containing at least one same solid acid catalyst. Preferably, the catalytic reactor contains two reaction zones.

At the inlet to each of said reaction zones, at least one fraction of the total quantity of olefins necessary for the alkylation reaction of the aromatic compound, preferably benzene, with the $C_9$–$C_{16}$, preferably $C_{10}$–$C_{14}$ linear olefin(s) is introduced.

Each of said fractions can be mixed with paraffins, in particular $C_9$–$C_{16}$, preferably $C_{10}$–$C_{14}$ paraffins. The inlet to each of the reaction zones is determined by the level of introduction of each of the olefin fractions. The introduction of each of the olefin fractions can, for example, be done by lateral injection into the reactor in a zone situated between two successive reaction zones.

According to the process of the invention, at the inlet to the first reaction zone of the catalytic reactor is introduced at least part, preferably all of the aromatic compound to be alkylated and a charge containing a first fraction of at least one linear olefin comprising from 9 to 16 carbon atoms per molecule, preferably from 10 to 14 carbon atoms per molecule, the charge being able to contain paraffins, in particular $C_9$–$C_{16}$, preferably $C_{10}$–$C_{14}$ paraffins. A second fraction of said $C_9$–$C_{16}$, preferably $C_{10}$–$C_{14}$ olefin(s) is then introduced at the inlet to the second reaction zone of the catalytic reactor, where it is mixed with at least part of the effluents originating from the first reaction zone. For a catalytic reactor having n reaction zones, an nth fraction of said olefin(s) is introduced at the inlet to the nth reaction zone of the catalytic reactor, where it is mixed with at least part of the effluents originating from the (n−1)th reaction zone. At least part of the effluents originating from the (n−1)th reaction zone is introduced at the inlet to the nth reaction zone of the catalytic reactor, the other part being able to be sent directly towards the outlet of the reactor. Preferably, the quantity of olefin(s) contained in each of the fractions introduced at the inlet to each of the reaction zones is such that approximately all of said olefin(s) are consumed in the reaction zone where the olefin(s) fraction has been introduced. Preferably, according to the process of the invention, at the inlet to at least one reaction zone, an olefins fraction is introduced in a quantity such that the aromatic compound(s)/olefins ratio is comprised between 21 and 50, preferably between 25 and 50 and very preferably between 25 and 45, in said reaction zone. The quantity of olefins contained in each of the fractions introduced into each of the reaction zones can vary according to the fractions by is never zero. In order to be able to even better control the aromatic compound(s)/olefins ratio in each of the reaction zones, it can be advantageous if said aromatic compound is introduced at the inlet to each of the reaction zones for which it is desired to obtain a determined aromatic compound(s)/olefins ratio. The total quantity of aromatic compound(s) to be introduced into the reactor in order to carry out the alkylation reaction is then distributed to the inlets of the different reaction zones for which it is desired to obtain a determined aromatic compound(s)/olefins ratio.

According to a first embodiment of the invention, the olefins fraction introduced at the inlet to each of said reaction zones is such that the aromatic compound(s)/olefins ratio in each of said reaction zones is comprised between 21 and 50, preferably between 25 and 50 and very preferably between 25 and 45. Advantageously, the olefins fraction introduced at the inlet to each of said reaction zones is such that the aromatic compound(s)/olefins ratio is identical in each of said reaction zones. A person skilled in the art will then adjust the quantity of olefins in each olefins fraction. It is also very advantageous that the olefins fraction introduced in each of said reaction zones represents 1/n of the total quantity of olefins necessary for the alkylation reaction, where n represents the number of reaction zones with n≧2. For example, for a catalytic reactor with 3 reaction zones, it is advantageous if one-third of the total quantity of linear olefins necessary for the alkylation reaction is introduced at the inlet to the first reaction zone, if a second third is introduced at the inlet to the second reaction zone, and if a third is introduced at the inlet to the third reaction zone.

According to a second embodiment of the invention, the olefins fraction introduced at the inlet to each of said reaction zones is such that the aromatic compound(s)/olefins ratio is different in at least two reaction zones, successive or not successive. Preferably, at the inlet to at least one reaction zone, an olefins fraction is introduced in a quantity such that the aromatic compound(s)/olefins ratio is greater than 50 in said reaction zone. Very preferably, at the inlet to at least one reaction zone, an olefins fraction is introduced in a quantity such that the aromatic compound(s)/olefins ratio is comprised between 21 and 50, preferably between 25 and 50 and very preferably between 25 and 45 in said reaction zone and, at the inlet to at least one other reaction zone, distinct from the preceding zone, an olefins fraction is introduced in a quantity such that the aromatic compound(s)/olefins ratio is greater than 50, preferably greater than 70 and very preferably greater than 100. This configuration according to which the aromatic compound(s)/olefins ratio is greater than 50, preferably greater than 70 and very preferably greater than 100, in at least one reaction zone is particularly useful when it is a question of limiting the deactivation and/or regenerating the solid acid catalyst present in said reaction zone, said catalyst being deactivated during the alkylation reaction carried out in said reaction zone, for example when the catalytic reactor has a configuration such as that described in the first embodiment of the invention, i.e. an aromatic compound(s)/olefins ratio comprised between 21 and 50 in each of the reaction zones. According to this second embodiment of the invention, the olefin(s) is(are) introduced in a low quantity at the inlet to the reaction zone containing the catalyst to be regenerated such that the aromatic compound(s)/olefins ratio is greater than 50; the aromatic compound(s) is(are) thus found to be present as a majority quantity, performing the function of desorbing hydrocarbon species adsorbed at the surface of the deactivated catalyst. Once the regeneration has been carried out, it is preferable that said zone having functioned in regeneration mode returns to its function carrying out the alkylation reaction. This can be achieved by injecting at the inlet to said reaction zone a fraction of $C_9$–$C_{16}$, preferably $C_{10}$–$C_{14}$ linear olefins in a quantity such that the aromatic compound(s)/olefins ratio is comprised between 21 and 50, preferably between 25 and 50 and very preferably between 25 and 45.

In general, the alkylation reaction carried out in the catalytic reactor implemented for the process of the invention is followed, at the outlet of said reactor, by at least one stage of separation of excess reagents. It can also be advantageously followed by at least one stage of separation of the monoalkylated compounds, i.e. 2-, 3-, 4-, 5- and 6-phenylalkane isomers, originating from the reaction, polyalkylated compounds (poly-alkylbenzenes). More precisely, at the outlet of the reactor, in general the product obtained is fractionated in order to separately collect a first effluent containing the aromatic compound, preferably benzene, which is non-converted, a second effluent containing at least one $C_9$–$C_{16}$, preferably $C_{10}$–$C_{14}$ linear olefin, which is non-converted, as well as the paraffins which are initially optionally present in the charge, a third effluent containing 2-, 3-, 4-, 5- and 6-phenylalkanes and a fourth effluent containing at least one poly-alkybenzene (or poly-alkylbenzene fraction), the latter being optionally, at least in part, recycled towards at least one of the n reaction zones, preferably towards the first reaction zone, where it reacts with the aromatic compound, preferably benzene, in contact with the solid acid catalyst present, in order to be at least in part translkylated (transalkylation reaction), and a mixture of 2-, 3-, 4-, 5- and 6-phenylalkanes is collected.

The operating conditions used in each of the reaction zones of the catalytic reactor used for implementation of the process according to the invention are chosen by a person skilled in the art as a function of the structure of the catalyst. Each of the reaction zones of the reactor is operated at a temperature usually below 400° C., preferably below 350° C., and very preferably below 300° C. and under a pressure of 1 to 10 MPa, preferably from 2 to 6 MPa, with a liquid hydrocarbon flow rate (space velocity) of approximately 0.5 to 80, preferably from 0.5 to 50 volumes per volume of catalyst and per hour. It can also be advantageous to operate under supercritical conditions.

According to the invention, the solid acid alkylation catalyst can be crystallized or amorphous. It can in particular be a catalyst comprising at least one zeolite of crystalline structure, for example having a structure as defined in the Classification "Atlas of Zeolite Framework Type" (W. M. Meier, D. H. Olson and Ch. Baerlocher, 5th revised edition, 2001, Elsevier). Preferably, the catalyst comprises at least one zeolite chosen from the group constituted by zeolites of the FAU, MOR, MTW, OFF, MAZ, BEA and EUO structural type. Amongst the zeolites of FAU structural type, the Y zeolite and the Y zeolite exchanged with rare earths (REY) are preferred. Amongst the zeolites of MOR structural type, the mordenite zeolite is preferred. Amongst the zeolites of MTW structural type, the ZSM-12 zeolite is preferred. Amongst the zeolites of OFF structural type, the offretite zeolite is preferred. Amongst the zeolites of MAZ structural type, the ZSM-4 zeolite is preferred. Amongst the zeolites of BEA structural type, the beta is zeolite preferred and amongst the zeolites of EUO structural type, the EU-1 zeolite is preferred. The solid acid catalyst contained in each of the reaction zones of the reactor used for the implementation of the process according to the invention can, when it is amorphous, contain a silica-alumina type solid.

Preferably, the solid acid catalyst contained in each of the reaction zones of the catalytic reactor used for the implementation of the process according to the invention comprises at least one Y zeolite, advantageously a dealuminated Y zeolite with an overall Si/Al atomic ratio greater than 4, preferably comprised between 8 and 79 and, still more advantageously comprised between 15 and 50. The dealuminated Y zeolite is generally used in mixture with at least one binding agent or a matrix generally chosen from the group formed by clays, aluminas, silica, magnesia, zirconium, titanium oxide, boron oxide and any combination of at least two of these oxides such as silica-alumina, silica-magnesia. All the known methods of agglomeration and shaping are applicable, such as, for example, extrusion, pelleting, coagulation into drops etc. The catalyst contained in each of the reaction zones of the reactor generally contains from 1 to 100%, preferably from 20 to 98%, very preferably from 40 to 98% of said dealuminated Y zeolite, and from 0 to 99%, preferably from 2 to 80% and, for example, from 2 to 60% by weight of a binding agent or a matrix. The dealuminated Y zeolites and their preparation are known. Reference can for example be made to U.S. Pat. No. 4,738,940

The Y zeolite, dealuminated or not, used in the process according to the invention is preferably at least partially in acid form (HY zeolite) and is characterized by different specifications:

an overall Si/Al atomic ratio greater than 4, preferably comprised between 8 and 70 and still more advantageously comprised between 15 and 50, a sodium content below 0.25% by weight, a crystalline paraffin with a unit cell smaller than $24.55.10^{-10}$ m and, preferably comprised between $24.20.10^{-10}$ m and $24.39.10^{-10}$ m,

- a specific surface area determined by the B.E.T. method greater than approximately 300 m²/g and preferably greater than approximately 450 m²/g.
- a water vapour adsorption capacity at 25° C., for a partial pressure of 3.46 mbar (millibar), greater than approximately 0.5% and preferably greater than approximately 3%.

The dealuminated Y zeolites are for example synthesized, generally starting with an NaY zeolite, by an appropriate combination of two basic treatments: (a) a hydrothermal treatment which combines temperature, the temperature being preferably comprised between 450 and 900° C. and very preferentially between 550 and 800° C., and partial water vapour pressure (40 to 100% of water vapour), and (b) an acid treatment by, preferably, a strong and concentrated mineral acid (0.01 to 10 N). Stage (a) is however only optional. Generally the NaY zeolite from which the Y zeolite used in the catalyst present in each of the reaction zones is prepared, has an overall Si/Al atomic ratio comprised between approximately 1.8 and 3.5; it is advisable beforehand to reduce the sodium content by weight to less than 3% and, preferably, to less than 2.5%. The reduction of the sodium content can be carried out by ion exchange of the NaY zeolite in solutions of ammonium salt (nitrate, sulphate, oxalate etc.) with an ammonium concentration comprised between 0.01 and 10 N, at a temperature comprised between 10 and 180° C. (optionally exchange under autogenous pressure), for a period of more than approximately 10 minutes. The NaY zeolite moreover generally possesses a specific surface area between approximately 750 and 950 m²/g.

Another preferred method of the invention consists of using as solid acid catalyst in each of the reaction zones a mixture of zeolites. It may be for example a mixture of zeolites constituted by at least one Y zeolite such as described previously and at least one zeolite of MOR structural type, in particular a mordenite zeolite.

With respect to the preparation of a catalyst comprising a mixture of zeolites, the mixture of said zeolites, which are found in powder state, is produced by all the powder mixing techniques known to a person skilled in the art, and followed by shaping. When the mixing of the zeolite powders is finished, the mixture is shaped by any technique known to a person skilled in the art. It can in particular be mixed with a matrix, generally amorphous, for example a moist alumina gel powder. The shaping can also be carried out with matrices other than alumina, such as for example magnesia, amorphous silica-aluminas, natural clays (kaolin, bentonite, sepiolite, attapulgite), silica, titanium oxide, boron oxide, zirconium, aluminium phosphates, titanium phosphates, zirconium phosphates, charcoal and their mixtures. Mixtures of alumina and silica, mixtures of alumina and silica-alumina, mixtures can also advantageously be used. It is preferred to use matrices containing alumina, in all its forms known to a person skilled in the art, and yet more preferably gamma alumina. The mixture is then shaped. Several techniques can be used for this purpose, and in particular extrusion through a die, pelleting and dragée production. The mixture of zeolites can also be constituted by a mixture of zeolites already shaped as described previously.

The catalyst contained in each of the reaction zones of the catalytic reactor for the implementation of the process according to the invention is shaped in the form of grains of different shapes and dimensions. It is used in general in the form of cylindrical or polylobate extrudates such as straight or twisted bilobates, trilobates, polylobates, but can optionally be produced and used in the form of crushed powder, tablets, rings, beads or disks.

After the shaping stage, the product obtained is subjected to a drying stage at a temperature comprised between 100 and 300° C., preferably between 120 and 200° C., then to a calcination stage at a temperature comprised between 350 and 650° C., preferably between 450 and 600° C.

The solid acid catalyst contained in each of the reaction zones of the catalytic reactor used for the implementation of the process according to the invention preferably comprises a Y zeolite, a mordenite zeolite or a mixture of zeolites constituted by at least one Y zeolite and at least one mordenite zeolite. The preparation of the zeolites of MOR structural type is known in the state of the art (U.S. Pat. No. 4,503,023).

The invention will be better understood on reading the following detailed example, which is non-limitative, of a particular embodiment of a device allowing the implementation of the process according to the invention (FIG. 1).

Fresh benzene arriving by the pipe 1 is mixed with benzene coming, by the pipe 10, from the head of a first fractionating column 9 and with a mixture comprising $C_9$–$C_{16}$, preferably $C_{10}$–$C_{14}$ linear olefins and $C_9$–$C_{16}$, preferably $C_{10}$–$C_{14}$ paraffins, by the pipe 2. The total mixture obtained constitutes the charge of an alkylation reactor 6. Said charge first passes through a heat exchanger 3, where it is preheated by indirect heat exchange with an effluent originating from the alkylation reactor 6. The charge is then sent, after its stay in the heat exchanger 3, into the alkylation reactor 6 by the pipe 4. The alkylation reactor 6 comprises two distinct reaction zones A and B, each containing the same solid alkylation catalyst, i.e. in the case of a zeolitic catalyst, the same crystalline nature of the zeolite for each of the catalysts and the same chemical composition (identical Si/Al ratio).

A second mixture constituted by at least one of the $C_9$–$C_{16}$, preferably $C_{10}$–$C_{14}$ linear olefins, accompanied by $C_9$–$C_{16}$, preferably $C_{10}$–$C_{14}$ paraffins, is introduced by the pipe 5 directly into the reactor 6, the injection point being situated between the two reaction zones A and B.

At the outlet of the reactor 6, the effluent is sent, by the pipe 7, to the heat exchanger 3, then, via the pipe 8, towards a first fractionating column 9. At the head of this first fractionating column 9, the majority of the excess benzene which has not reacted is extracted and recycled by the pipe 10. At the base of this first fractionating column 9, a fraction is collected which is sent, by the pipe 11, towards a second fractionating column 12. At the head of this second fractionating column 12, mostly the non-converted $C_9$–$C_{16}$, preferably $C_{10}$–$C_{14}$ linear olefins, as well as the paraffins initially present in the charge are collected, by the pipe 13. At the base of this second fractionating column 12 a mixture is drawn off, which is sent, by the pipe 14, towards a third fractionating column 15. At the head of this third fractionating column 15, mostly a mixture of 2-phenylalkane, 3-phenylalkane, 4-phenylalkane, 5-phenylalkane, and 6-phenylalkane is collected, which is sent to storage by the pipe 16. At the base of this third fractionating column 15, mostly dialkylbenzenes are drawn off, by the pipe 17, which can be at least in part be recycled towards at least one of the two reaction zones (not represented in the figure).

Examples 1 to 6, given by way of illustration, will allow a person skilled in the art to better understand the present invention:

EXAMPLE 1

Preparation of Catalyst A Containing a Dealuminated Y Zeolite

An NaY zeolite of formula $NaAlO_2(SiO_2)_{2.5}$ is used as raw material. This zeolite is subjected to 5 successive exchanges in ammonium nitrate solutions at a concentration of 2 N, at a temperature of 95° C., over a period of 2 hours, and with a volume of solution to weight of zeolite ratio equal to 8 cm$^3$/g. The sodium content in the $NH_4Y$ zeolite obtained is 0.83% by weight. This product is then rapidly introduced into an oven preheated to 770° C. and left for 4 hours in a static atmosphere (100% water vapour). The zeolite is then subjected to an acid treatment under the following conditions: the ratio of volume of 3N nitric acid to the weight of solid is equal to 9 cm$^3$/g, the temperature is 95° C. and the duration of the treatment 3 hours. Then another treatment under the same conditions is carried out, but with an 0.5N nitric acid solution.

The zeolite thus obtained has a sodium content by weight of 0.14% and an Si/Al atomic ratio equal to 38.

The zeolite is shaped by extrusion with alumina (50% zeolite and 50% alumina). The extrudates are then dried, then calcinated at 550° C.

EXAMPLE 2

Preparation of Catalyst B Containing a Mordenite Zeolite

A mordenite zeolite in sodium form is used, the chemical formula of which in the hydride state is $NaAlO_2(SiO_2)_{5.1}$, and its sodium content is 5% by weight. 100 grams of this powder are taken to reflux at 100° C. for 2 hours in a solution of 4N ammonium nitrate with a V/W ratio equal to 4 cm$^3$/g. This cation exchange operation is repeated 3 times. The sodium content by weight of the product obtained is approximately 500 ppm (part per million).

This product is then subjected to an acid attack using an aqueous solution of 4.5N nitric acid, the product is taken to reflux in this aqueous solution for 2 hours with a V/W ratio equal to 4 cm$^3$/g. After this treatment, the product is washed in demineralized water.

The mordenite obtained has an Si/Al atomic ratio equal to 40 and a sodium content equal to 20 ppm by weight.

The mordenite thus obtained is then mixed with an alumina gel (50% by weight of mordenite and 50% by weight of alumina gel). The mixture obtained is shaped in the form of extrudates with a diameter equal to approximately 1.8 mm by passing through a die. The extrudates are then dried in an oven at 120° C. overnight, then calcinated under dry air at 550° C.

EXAMPLE 3

Alkylation of Benzene by 1-dodecene in the Presence of Catalyst A (Not According to the Invention)

A catalytic reactor is used, comprising only one reaction zone containing 50 cm$^3$ of catalyst A in the form of extrudates, prepared according to Example 1.

The operating conditions for the alkylation of the benzene by 1-dodecene are the following:
 temperature: 135° C.
 pressure: 4 MPa
 HVR=1 h$^1$ (cm$^3$ benzene+1-dodecene charge per cm$^3$ of catalyst and per hour)
 benzene/1-dodecene molar ratio: 30

A charge is prepared containing 72% by weight of benzene and 28% by weight of 1-dodecene. This charge is introduced at the inlet to the catalytic reactor where the alkylation reaction is carried out.

The results obtained are presented in Table 1.

TABLE 1

| | |
|---|---|
| Duration of cycle with conversion of the olefin > 95% | 15 h |
| Linearity of the product obtained (% by weight) | 92.8 |
| 2-phenylalkane | 27.1 |
| 3-phenylalkane | 22.3 |
| 4-phenylalkane | 19.4 |
| 5-phenylalkane | 12.6 |
| 6-phenylalkane | 11.7 |
| didodecylbenzene (% by weight) | 5.3 |
| heavy residue (% by weight) | 1.5 |

The linearity is defined as being equal to the mass ratio [LAB/(LAB+BAB)], the LABs being the linear alkylbenzenes and the BABs the branched alkylbenzenes, i.e ramified. The 2-phenylalkane, 3-phenylalkane, 4-phenylalkane, 5-phenylalkane, 6-phenylalkane mixture contains both LABs and BABs.

EXAMPLE 4

Alkylation of Benzene by 1-dodecene in the Presence of Catalyst A (According to the Invention)

A catalytic reactor is used, in which two reaction zones are present each containing 25 cm$^3$ of catalyst A in the form of extrudates, prepared according to Example 1.

The operating conditions for the alkylation of the benzene by 1-dodecene are the following:
 temperature: 135° C.
 pressure: 4 MPa
 HVR=1 h$^{-1}$ (cm$^3$ benzene+1-dodecene charge per cm$^3$ of catalyst and per hour)
 benzene/1-dodecene molar ratio: 30

A charge is prepared containing 86% by weight of benzene and 14% by weight of 1-dodecene. This charge which is introduced at the inlet to the first reaction zone contains all of the benzene necessary for the alkylation reaction and half of the quantity of 1-dodecene necessary for the alkylation reaction. The other half, corresponding to a quantity of 1-dodecene identical to that present in the charge introduced at the inlet to the first zone, is introduced at the inlet to the second reaction zone by a lateral injection at the middle of the catalytic reactor.

The results obtained are presented in Table 2.

TABLE 2

| | |
|---|---|
| Duration of cycle with conversion of the olefin > 95% | 26 h |
| Linearity of the product obtained (% by weight) | 94.3 |
| 2-phenylalkane | 28.3 |
| 3-phenylalkane | 23.1 |
| 4-phenylalkane | 19.9 |
| 5-phenylalkane | 13.1 |
| 6-phenylalkane | 12.1 |
| didodecylbenzene (% by weight) | 2.8 |
| heavy residue (% by weight) | 0.7 |

The introduction of the 1-dodecene into two distinct reaction zones leads to an extension of the duration of the alkylation reaction cycle, which increases from 15 hours to 26 hours for the same total quantity of 1-dodecene introduced into the catalytic reactor. Each of the catalysts present in each of the two reaction zones (Example 4) is deactivated less rapidly than the catalyst present in the single reaction zone (Example 3). Moreover, the use of a reactor comprising two reaction zones each containing a solid acid catalyst (dealuminated Y zeolite) leads to an alkylation product the linearity of which is improved, which is advantageous for a subsequent use in the manufacture of detergents.

EXAMPLE 5

Alkylation of Benzene by 1-dodecene in the Presence of a Mixture of Catalyst A+B (Not According to the Invention)

A reactor is used, comprising only one reaction zone containing 50 cm$^3$ of catalyst constituted by 50% of catalyst A and 50% of catalyst B in the form of extrudates, prepared according to Example 1 and 2.

The operating conditions for the alkylation of the benzene are those described in Example 3.

A charge is prepared containing 72% by weight of benzene and 28% by weight of 1-dodecene. This charge which is introduced at the inlet to the catalytic reactor where the alkylation reaction is carried out.

The results obtained are presented in Table 3.

TABLE 3

| | |
|---|---|
| Duration of cycle with conversion of the olefin > 95% | 22 h |
| Linearity of the product obtained (% by weight) | 93.2 |
| Composition of the product obtained (% by weight) | |
| 2-phenylalkane | 50.1 |
| 3-phenylalkane | 24.6 |
| 4-phenylalkane | 9.2 |
| 5-phenylalkane | 4.6 |
| 6-phenylalkane | 3.7 |
| didodecylbenzene (% by weight) | 6.8 |
| heavy residue (% by weight) | 1.2 |

EXAMPLE 6

Alkylation of Benzene by 1-dodecene in the Presence of a Mixture of Catalysts A+B (According to the Invention)

A catalytic reactor is used, in which two reaction zones are present each containing 25 cm$^3$ of catalyst constituted by 50% of catalyst A and 50% of catalyst B in the form of extrudates, prepared according to Example 1 and 2.

The operating conditions for the alkylation of the benzene are those described in Example 4.

A charge is prepared containing 86% by weight of benzene and 14% by weight of 1-dodecene. This charge which is introduced at the inlet to the first reaction zone contains all of the benzene necessary for the alkylation reaction and half of the quantity of 1-dodecene necessary for the alkylation reaction. The other half, corresponding to a quantity of 1-dodecene identical to that present in the charge introduced at the inlet to the first zone, is introduced at the inlet to the second reaction zone by a lateral injection at the middle of the catalytic reactor.

The results obtained are presented in Table 4.

TABLE 4

| | |
|---|---|
| Duration of cycle with conversion of the olefin > 95% | 28 h |
| Linearity of the product obtained (% by weight) | 95.6 |
| Composition of the product obtained (% by weight) | |
| 2-phenylalkane | 51.1 |
| 3-phenylalkane | 25.2 |

TABLE 4-continued

| | |
|---|---|
| 4-phenylalkane | 10.7 |
| 5-phenylalkane | 5.1 |
| 6-phenylalkane | 4.2 |
| didodecylbenzene (% by weight) | 3.1 |
| heavy residue (% by weight) | 0.6 |

The introduction of the 1-dodecene into two distinct reaction zones leads to an extension of the duration of the alkylation reaction cycle, which increases from 22 hours to 28 hours for the same total quantity of 1-dodecene introduced into the catalytic reactor. Each of the catalysts present in each of the two reaction zones (Example 6) is deactivated less rapidly than the catalyst present in the single reaction zone (Example 5). Moreover, the use of a reactor comprising two reaction zones each containing a solid acid catalyst (dealuminated Y zeolite in a mixture with a mordenite zeolite) leads to an alkylation product the linearity of which is improved, which is advantageous for a subsequent use in the manufacture of detergents.

The invention claimed is:

1. A process for the production of at least one phenylalkane comprising conducting an alkylation reaction of at least one aromatic compound with at least one linear olefin having from 9 to 16 carbon atoms per molecule, said reaction being carried out in a catalytic reactor in which n reaction zones are present each containing at least one same solid acid catalyst, n being greater than or equal to 2, and introducing at the inlet to each reaction zone at least one fraction of the total quantity of olefins necessary for said reaction.

2. A process according to claim 1 wherein at the inlet to at least one reaction zone, an olefins fraction is introduced in a quantity such that the aromatic compound(s)/olefins ratio is comprised between 21 and 50 in said reaction zone.

3. A process according to claim 1 wherein the olefins fraction introduced at the inlet to each of said reaction zones is such that the aromatic compound(s)/olefins ratio is comprised between 21 and 50 in each of said reaction zones.

4. A process according to claim 3 wherein the aromatic compound(s)/olefins ratio is comprised between 25 and 45 in each of said reaction zones.

5. A process according to claim 3 wherein the olefins fraction introduced at the inlet to each of said reaction zones is such that the aromatic compound(s)/olefins ratio is identical in each of said reaction zones.

6. A process according to claim 3 wherein the olefins fraction introduced at the inlet to each of said reaction zones represents 1/n of the total quantity of olefins necessary for the alkylation reaction, with n>2.

7. A process according to claim 1 wherein the olefins fraction introduced at the inlet to each of said reaction zones is such that the aromatic compound(s)/olefins ratio is different in at least two reaction zones.

8. A process according to claim 7 wherein at the inlet to at least one reaction zone, an olefins fraction is introduced in a quantity such that the aromatic compound(s)/olefins ratio is greater than 50 in said reaction zone.

9. A process according to claim 1 wherein the aromatic compound is benzene.

10. A process according to claim 1 wherein the solid acid catalyst comprises at least one zeolite of the FAU, MOR, MTW, OFF, MAZ, BEA and EUO structural types.

11. A process according to claim 10 wherein said solid acid catalyst comprises a Y zeolite, a mordenite zeolite or a mixture of zeolites constituted by at least one Y zeolite and at least one mordenite zeolite.

12. A process according to claim 1 wherein the linear olefin is an olefin having from 10 to 14 carbon atoms per molecule.

13. A process according to claim 1 further comprising after said alkylation reaction, at the outlet from said reactor at least one stage of separation of the excess reagents.

14. A process according to claim 1 further comprising reacting the at least one phenylalkane to form a detergent.

15. A process according to claim 2 wherein the olefins fraction introduced at the inlet to each of said reaction zones is such that the aromatic compound(s)/olefins ratio is different in at least two reaction zones.

16. A process according to claim 15 wherein at the inlet to at least one reaction zone, an olefins fraction is introduced in a quantity such that the aromatic compound(s)/olefins ratio is greater than 50 in said reaction zone.

17. A process according to claim 15 wherein the solid acid catalyst comprises at least one zeolite of the FAU, MOR, MTW, OFF, MAZ, BEA and EUO structural types.

18. A process according to claim 17 wherein said solid acid catalyst comprises a Y zeolite, a mordenite zeolite or a mixture of zeolites constituted by at least one Y zeolite and at least one mordenite zeolite.

19. A process according to claim 14 wherein said further reacting comprises sulfurization.

* * * * *